US011744577B2

(12) United States Patent
Fancey et al.

(10) Patent No.: US 11,744,577 B2
(45) Date of Patent: Sep. 5, 2023

(54) SUTURE THREAD PRODUCTS

(71) Applicant: THE UNIVERSITY OF HULL, Hull (GB)

(72) Inventors: Kevin S Fancey, Hull (GB); Louise A France, Hull (GB)

(73) Assignee: THE UNIVERSITY OF HULL, Hull (GB)

( * ) Notice: Subject to any disclaimer, the term of this patent is extended or adjusted under 35 U.S.C. 154(b) by 379 days.

(21) Appl. No.: 15/733,613

(22) PCT Filed: Mar. 14, 2019

(86) PCT No.: PCT/EP2019/056393
§ 371 (c)(1),
(2) Date: Sep. 15, 2020

(87) PCT Pub. No.: WO2019/175297
PCT Pub. Date: Sep. 19, 2019

(65) Prior Publication Data
US 2021/0022735 A1  Jan. 28, 2021

(30) Foreign Application Priority Data
Mar. 15, 2018 (GB) ...................................... 1804141

(51) Int. Cl.
A61B 17/06 (2006.01)
A61B 17/00 (2006.01)

(52) U.S. Cl.
CPC .. A61B 17/06123 (2013.01); A61B 17/06166 (2013.01); A61B 2017/00526 (2013.01);
(Continued)

(58) Field of Classification Search
CPC ........ A61B 17/06123; A61B 17/06166; A61B 2017/00526; A61B 2017/00884; A61B 2017/0618
See application file for complete search history.

(56) References Cited

U.S. PATENT DOCUMENTS 3,454,011 A    7/1969  Wagner
4,621,638 A   11/1986  Silvestrini
(Continued)

FOREIGN PATENT DOCUMENTS

WO    1992012673 A1    8/1992
WO    2006008163       1/2006
(Continued)

OTHER PUBLICATIONS

International Search Report and Written Opinion dated Jun. 24, 2019, in related PCT Application No. PCT/EP2019/056393.
(Continued)

Primary Examiner — Phong Son H Dang
(74) Attorney, Agent, or Firm — MASCHOFF BRENNAN

(57) ABSTRACT

There is provided a product comprising a suture thread which, prior to being used to form a surgical suture, is in a stressed state which gives the suture thread a tendency to undergo lengthwise viscoelastic contraction. The suture thread undergoes viscoelastic contraction when in use as a surgical suture and this may promote wound healing to a greater extent than a conventional suture thread which does not undergo viscoelastic contraction.

12 Claims, 5 Drawing Sheets

(52) U.S. Cl.
CPC ............... *A61B 2017/00884* (2013.01); *A61B 2017/0618* (2013.01)

(56) References Cited

U.S. PATENT DOCUMENTS

| | | | |
|---|---|---|---|
| 5,102,419 A | | 4/1992 | Gertzman et al. |
| 5,349,044 A | * | 9/1994 | Liu ................... A61L 17/04 606/228 |
| D744,648 S | * | 12/2015 | Wentling ................. D24/145 |
| 11,504,113 B2 | * | 11/2022 | Kim ................ A61B 17/06166 |
| 2008/0075749 A1 | * | 3/2008 | Dyer ..................... A61K 8/8123 424/422 |
| 2010/0084294 A1 | * | 4/2010 | Kirsch ............. A61B 17/06166 206/370 |
| 2011/0046669 A1 | * | 2/2011 | Goraltchouk ............ D02J 3/10 606/228 |
| 2011/0125188 A1 | * | 5/2011 | Goraltchouk ......... D06M 15/00 606/228 |
| 2018/0206842 A1 | * | 7/2018 | Wentling ......... A61B 17/06133 |

FOREIGN PATENT DOCUMENTS

| | | |
|---|---|---|
| WO | 2009132284 A2 | 10/2009 |
| WO | 2016014579 A1 | 1/2016 |

OTHER PUBLICATIONS

Metz S A et al, "Stress relaxation of organic suture materials", Apr. 1, 1990 (Apr. 1, 1990), vol. 11, No. 3, p. 197-199, XP024142855,DOI: 10.1016/0142-9612(90)90155-J, ISSN:0142-9612 [retrieved on Apr. 1, 1990], See Results, Discussion;figures 1, 2.

Masamitsu Hasegawa et al., "Rheological Characteristics of Surgical Sutures III Static Viscoelasticities of Surgical Sutures", DOI: https://doi.org/10.1678/rheology1973.13.3_131, Sep. 20, 1985 (Sep. 20, 1985), p. 131-136, Retrieved from the Internet: URL:https://www.jstage.jst.go.jp/article/rheology1973/13/3/13_131/_pdf/-char/ja, XP055596214 DOI: https://doi.org/10.1678/rheology1973.13.3_131, [retrieved on Jun. 13, 2019] 1-33, figures 1-6; tables 1-2.

Von Fraunhofer J A et al, "Characterization of surgical suture materials using dynamic mechanical analysis", Jan. 1, 1992 (Jan. 1, 1992), vol. 13, No. 10, p. 715-720, XP024142652, DOI: 10.1016/0142-9612(92)90133-9, ISSN:0142-9612 , [retrieved on Jan. 1, 1992], 1-33, See Abstract, Conclusions and Appendix.

Vizesi F et al, "Stress Relaxation and Creep: Viscoelastic Properties of Common Suture Materials Used for Flexor Tendon Repair", Feb. 1, 2008 (Feb. 1, 2008), vol. 33, No. 2, p. 241-246, XP022585045, DOI: 10.1016/J.JHSA.2007.10.011, ISSN:0363-5023, [retrieved on Feb. 19, 2008], 1-33, cited in the application, See Abstract and Discussion;figures 1-4.

UK IP Office Search Report and Written Opinion dated Aug. 22, 2018, in related UK Application No. GB1804141.8.

Hurwit et al., "Viscoelastic Properties of Common Suture Material Used for Rotator Cuff Repair and Arthroscopic Procedures", Arthroscopy, vol. 30, Nov. 2014, p. 1406-1412.

Romanyk et al., "Viscoelastic response of the midpalatal suture during maxillary expansion treatment", Orthodontics & craniofacial research, vol. 19, Feb. 2016, p. 28-35.

Vizesi et al., "Stress relaxation and creep: viscoelastic properties of common suture materials used for flexor tendon repair", The Journal of hand surgery, vol. 33, Feb. 2008, p. 241-246.

* cited by examiner

SUTURE THREAD PRODUCTS

FIELD

The invention relates to products comprising a suture thread, to methods of manufacturing products comprising a suture thread and to a viscoelastic solid substance for use in a method of surgery.

BACKGROUND

A surgical suture is a stitch or a series or row of stitches applied to a tissue or tissues of a human or animal patient. Generally, the surgical suture holds together adjacent parts of a tissue or adjacent tissues of a patient to promote healing. A suture thread is a thread that is used to form a surgical suture.

Suture thread is available in many types and may be absorbable or non-absorbable, monofilament or multifilament. Once used to form a surgical suture, known suture thread generally remains at a constant length.

U.S. Pat. No. 3,454,011 proposes the use of spandex as a suture thread. It is suggested that the ability of spandex to undergo elastic expansion may be beneficial to wound healing as the surgical sutures would expand in response to swelling of the wound and thereby avoid laceration of the sutured tissue on swelling. U.S. Pat. No. 3,454,011 teaches that spandex threads exhibit viscoelastic behaviour in their load elongation properties.

WO 2006/008163 discloses recombinant spider silk protein and suggests that one of many possible uses for the recombinant protein would be as a suture thread. WO2006/008163 reports that the recombinant spider silk exhibits viscoelastic creep when subjected to a tensile force.

U.S. Pat. No. 5,102,419 discloses a polymeric suture thread which undergoes elastic elongation and it is suggested that the elastic elongation may be beneficial to wound healing as the surgical sutures would expand in response to swelling of the wound and thereby avoid laceration of the sutured tissue during swelling. U.S. Pat. No. 5,102,419 also teaches that the polymeric thread undergoes viscoelastic elongation when subjected to low stresses for short periods of time.

An article entitled "Viscoelastic Properties of Common Suture Material Used for Rotator Cuff Repair and Arthroscopic Procedures" by Hurwitt, D. et al. in Arthroscopy: The Journal of Arthroscopic and Related Surgery, Vol 30, No 11, pp 1406-1412 examines the propensity of commercial suture threads to undergo viscoelastic extension. The article suggests that suture threads which undergo lower degrees of viscoelastic extension are preferred for rotator cuff repair as this helps to minimise unwanted gap formation between the sutured tissues.

An article entitled "Stress Relaxation and Creep: Viscoelastic Properties of Common Suture Materials Used for Flexor Tendon Repair" by Vizesi, F. et al. in The Journal of Hand Surgery, Vol. 33, Issue 2, pp 241-246 also examines the propensity of commercial suture threads to undergo viscoelastic extension. The article suggests that suture threads which undergo lower degrees of viscoelastic extension are preferred for flexor tendon repair as this helps to minimise unwanted gap formation between the sutured tissues.

SUMMARY

Despite it having been known for many years that some suture threads exhibit viscoelastic properties during extension, it has not hitherto been appreciated that viscoelastic contraction of a suture thread may be clinically beneficial to healing of sutured tissues. Preferred aspects and embodiments of the present invention relate to products comprising suture threads which, before use, are in a stressed state giving them a tendency to undergo lengthwise viscoelastic contraction when in use as surgical sutures.

In accordance with a first aspect of the invention, there is provided a product comprising a suture thread and a package, the suture thread being sterile and being enclosed within the package so that the package maintains the suture thread sterile, the suture thread having a length, and being in a stressed state which gives the suture thread a tendency to undergo lengthwise viscoelastic contraction.

Preferably, the suture thread is maintained in said stressed state by a structure engaged with the suture thread so as to resist lengthwise viscoelastic contraction of the suture thread by application of a force to the suture thread. In one such embodiment, the structure is rigid, and the force is a reaction force opposing the force exerted by the viscoelastic contraction of the suture thread. The structure can be disengaged from the suture thread to allow lengthwise viscoelastic contraction of the suture thread when it is desired to use the suture thread to form a surgical suture. The structure may be part of the package.

Alternatively, the suture thread may be maintained in the stressed state by refrigeration which slows viscoelastic contraction.

In accordance with a second aspect of the invention, there is provided a product comprising a suture thread and a structure engaged with the suture thread, the suture thread having a length and two opposed ends, the suture thread being in a stressed state which gives the suture thread a tendency to undergo lengthwise viscoelastic contraction, said engagement resisting lengthwise viscoelastic contraction of the suture thread by application of a force to the suture thread and comprising the suture thread being wound around a portion of the structure and the two ends of the suture thread being secured to the structure, the structure being disengageable from the suture thread to allow lengthwise viscoelastic contraction of the suture thread when it is desired to use the suture thread to form a surgical suture.

The winding of the suture thread around a portion of the structure with the two ends of the thread being secured to the structure, allows the viscoelastic contraction of the suture thread to be resisted while, at the same time, the dimensions of the product may be much less than the length of the suture thread.

Preferably, the structure is rigid and the force is a reaction force opposing the force exerted by the viscoelastic contraction of the suture thread.

The structure may be part of a package within which the suture thread is enclosed. In this case, the suture thread may be sterile and the package maintains the sterility of the suture thread.

A suture thread of the first or second aspect of the invention may be used to form a surgical suture which undergoes viscoelastic contraction while applied to a patient. The contraction is lengthwise contraction of the suture thread which forms the stitch or stitches. The contraction applies a force to the tissue or tissues to which the surgical suture is applied. In many cases, the contraction will have the effect of pulling closer parts of a tissue or different tissues.

The viscoelastic contraction undergone by the suture thread while applied as a surgical suture may promote healing of the tissue or tissues to which the surgical suture is applied. Promotion of healing by the viscoelastic contraction may occur by a variety of mechanisms.

The application of force and/or movement, to a tissue or tissues, by the viscoelastic contraction, may itself promote healing, for example by attracting cells and/or causing cell proliferation. Healing may also be promoted by contact between adjacent tissues or parts of a tissue when they are brought together by the viscoelastic contraction of the suture thread. In addition, healing may be promoted by the surface properties of the suture thread of the invention, as discussed below. Hence, a suture thread that is in a stressed state which gives the suture thread a tendency to undergo lengthwise viscoelastic contraction may, in use, promote tissue healing to a greater extent as compared to known suture threads which do not undergo viscoelastic contraction. This may translate into faster healing of a wound.

A suture thread that is in a stressed state which gives the suture thread a tendency to undergo lengthwise viscoelastic contraction may also help to minimise scar formation by avoiding overtightening of surgical sutures. Because the suture thread undergoes lengthwise contraction, surgical sutures using the suture thread may be formed more loosely than would be the case if conventional suture thread was to be used. The lengthwise viscoelastic contraction would then act to tighten up the surgical suture slowly. This could be used to achieve a gradual closing of a wound and to avoid initial overtightening.

In many situations, optimum promotion of healing by the suture thread, when applied as a surgical suture, may be achieved when viscoelastic contraction of the suture thread continues over 1 to 6 weeks and has a magnitude which is sufficient to apply a therapeutically significant force and/or movement to the tissue or tissues during the healing period. In view of this, the suture thread preferably demonstrates the following characteristics in the following test, which is performed on the suture thread prior to use as a surgical suture (for example in a laboratory at a controlled temperature). Specifically, the suture thread, in the absence of applied force or treatment tending to resist lengthwise contraction, and when maintained at a temperature of 20° C., preferably undergoes lengthwise viscoelastic contraction lasting, at least, over a test period of time which is in the range of from 1 to 6 weeks and, over said period of time, the suture thread undergoes a degree of lengthwise viscoelastic contraction which is in the range of from 1% to 30% of the length of the suture thread. The period of time of the test may be chosen to be any time from 1 week to 6 weeks. For example, where it is anticipated that the suture thread will be used for suturing procedures where the surgical suture is left in place for no more than a week, then a test period of 1 week may be chosen. Longer test periods, up to 6 weeks, may be used where it is anticipated that the suture thread will be used for suturing procedures where the surgical suture is left in place for more than a week. As long as the suture thread undergoes lengthwise viscoelastic contraction in the range of from 1% to 30% of the length of the suture thread, and the viscoelastic contraction lasts over any chosen test period of time from 1 week to 6 weeks in duration, under the conditions defined above, the test is passed. For the purposes of the test, it does not matter whether the suture thread does or does not continue to undergo viscoelastic contraction after the chosen test period of time, and this applies whether the chosen test period of time is 1 week or 6 weeks or some intermediate period of time.

It is especially preferred that the degree of lengthwise viscoelastic contraction exhibited by the suture thread over the test period of time is in the range of 1% to 15% of the length of the suture thread. More preferably, the degree of lengthwise viscoelastic contraction exhibited by the suture thread over the test period of time is in the range of 2% to 15%, or 3% to 15% of the length of the suture thread. Most preferably, this value is in the range of 5% to 15% of the length of the suture thread. Alternatively, the degree of lengthwise viscoelastic contraction exhibited by the suture thread over the test period of time is at least 1%, or at least 2%, 3%, 4%, 5%, 6%, 7%, 8%, 9% or 10%. The test period of time could be, for example, 1, 2, 3, 4, 5, or 6 weeks.

Generally, the rate of viscoelastic contraction decreases over said period of time.

The laboratory test described above is performed at 20° C. for convenience and reproducibility. When a suture thread is used in practice to form a surgical suture, the temperature experienced by the surgical suture may be, for example, in the region of about 20° C. to 37° C. and will vary depending on a number of factors including the location of the surgical suture in/on the patient and on the ambient conditions.

The suture thread may be made from any viscoelastic solid material which is suitable for forming a thread and which is clinically acceptable for use as a suture thread. Many polymers, especially amorphous and partially crystalline polymers, are suitable. Preferably the suture thread comprises a material selected from the group consisting of: polyamide (especially nylon 6,6); polypropylene; polyethylene; ultra-high-molecular-weight polyethylene; high-density polyethylene; polyethylene terephthalate; rayon; and silk. The suture thread is preferably non-absorbable.

The suture thread will preferably have a diameter of between 0.01 and 2.0 mm, more preferably from 0.1 mm to 2.0 mm, and most preferably from 0.1 mm to 1.0 mm. Suture threads may be supplied conveniently in lengths of from 10 cm to 1 m.

The suture thread may be formed as a single filament. Alternatively, the suture thread may be made up of two or more filaments held together, such as by weaving, to form a thread.

As discussed above, the suture thread of the first or second aspect of the invention exists in a stressed state which gives the suture thread a tendency to undergo lengthwise viscoelastic contraction. The viscoelastic contraction occurs over a finite length of time and so is eventually exhausted. One possibility is that the suture thread is used to form a surgical suture sufficiently soon after manufacture of the suture thread so that the suture thread still has the capacity to undergo a satisfactory degree of lengthwise contraction over the desired time period. Preferably, however, the suture thread is maintained in the stressed state until it is desired to use the suture thread. This maintains, until use, some or all of the tendency to undergo lengthwise viscoelastic contraction.

One manner in which the stressed state can be maintained is to refrigerate the suture thread until it is desired to use it. The refrigeration maintains the stressed state by slowing the rate of viscoelastic contraction, so that when the suture thread is used to form a surgical suture (and no longer refrigerated) the suture thread still has most of, or at least a clinically sufficient proportion of, its initial tendency to undergo lengthwise viscoelastic contraction. In general, the degree to which viscoelastic contraction is retarded by refrigeration increases with decreasing refrigeration temperature over a given time period.

In the second aspect of the invention, and preferred embodiments of the first aspect, the suture thread is maintained in the stressed state by the structure engaged with the suture thread. Engaging the suture thread with a structure to maintain the stressed state does not necessarily maintain 100% of the initial capacity of the suture thread to undergo viscoelastic contraction. Even if viscoelastic contraction is prevented completely by and during the engagement, the capacity of the thread to undergo viscoelastic contraction when released from the structure may decrease over the time the thread is engaged with the structure due to stress relaxation effects. Loss of capacity to undergo viscoelastic contraction due to stress relaxation occurs slowly such that, in general, a suture thread can be stored in engagement with a structure for a useful period of time and still undergo a clinically useful degree of viscoelastic contraction when in use forming a surgical suture.

Preferably, in either the first or second aspect of the invention, the suture thread is attached to a needle suitable for suturing. The needle may be swaged to an end of the suture thread.

Preferably, the suture thread of the products of the first and second aspects of the invention has no tendency to undergo elastic contraction. Any tendency to undergo elastic contraction can be rapidly released simply by removing tensile stress from the suture thread before engaging the suture thread with a structure or enclosing the suture thread within a package.

The lengthwise viscoelastic contraction undergone by the suture thread of the first or second aspect of the invention is capable of generating a force. The force is most easily measured when the suture thread is formed into a loop. The loop is placed, without appreciable slack, between a fixed support and the attachment point of a force gauge; such that the loop has two generally parallel lengths connected by two arcuate ends of the loop which, respectively, loop around the fixed support and the attachment point. Preferably, when the contraction force is measured in this way at 20° C., the force generated over 100 hours is at least 0.1 N, and preferably at least 0.2 N, 0.3 N, 0.4 N, 0.5 N, or 1 N. The test may be performed conveniently with a loop of about 60 cm, although the length of the thread is not considered to be a major factor in generating a suitable force.

In accordance with a third aspect of the invention, there is provided a method of manufacturing a product comprising a suture thread, comprising: providing a thread having a length; applying to the thread a stressed state which gives the thread a tendency to undergo lengthwise viscoelastic contraction; and after said application of the stressed state, packing at least part of the length of the thread in a package to form a packaged suture thread, wherein the package is suitable for maintaining sterility of the suture thread and the suture thread is in a stressed state which gives the suture thread a tendency to undergo lengthwise viscoelastic contraction.

The method may also include refrigerating the suture thread in the package to maintain the suture thread in the stressed state.

In accordance with a fourth aspect of the invention, there is provided a method of manufacturing a product comprising a suture thread, comprising: providing a thread having a length; applying to the thread a stressed state which gives the thread a tendency to undergo lengthwise viscoelastic contraction, and after said application of the stressed state, engaging at least part of the length of the thread with a structure to form an engaged suture thread, said engagement with the structure maintaining the suture thread in a stressed state by resisting lengthwise viscoelastic contraction of the suture thread by application of a force to the suture thread, the structure being disengageable from the suture thread to allow lengthwise viscoelastic contraction of the suture thread when it is desired to use the suture thread to form a surgical suture.

In a preferred embodiment of the fourth aspect of the invention, engaging the suture thread with the structure comprises the suture thread being wound around a portion of the structure and the two ends of the suture thread being secured to the structure.

Preferably, the method of the fourth aspect of the invention includes packing the suture thread in a package wherein the package is suitable for maintaining sterility of the suture thread. The structure may be part of the package.

In either the third or fourth aspect of the invention, the thread to which the stressed state is applied will preferably be longer than typical lengths of suture thread that are supplied commercially. In this case, after the stressed state has been applied to the thread, the thread will preferably be cut into lengths more convenient for commercial supply. Each individual cut length may be referred to as a suture thread and may be packed within a respective package and/or engaged with a respective structure to maintain the suture thread in the stressed state. Each individual cut suture thread may be of a length convenient for use by a medical practitioner to form a surgical suture. Alternatively, individual cut suture threads may be of a length which will require further cutting before use.

Alternatively, the thread to which the stressed state is applied may be packed within a package and/or engaged with a structure to maintain the stressed state, without first cutting the thread. In this case, the whole thread will be referred to as a suture thread. In this case, the suture thread may be sufficiently long so that it is anticipated that it will be cut into more convenient lengths before use. Alternatively, although less desirable, the thread to which the stressed state is applied could be of a length convenient for use to form a surgical suture.

In either the third or fourth aspect of the invention, the suture thread will preferably be sterile. Sterilisation is preferably performed after packing the suture thread in a package.

The method of either the third or fourth aspect of the invention may also include attaching a needle to the suture thread.

The stressed state giving the suture thread a tendency to undergo lengthwise viscoelastic contraction may be applied by a method which comprises subjecting the thread to a lengthwise tensile force so that the thread extends by undergoing lengthwise viscoelastic creep. Viscoelastic creep is a time dependent increase in strain. Typically, the tensile force is maintained, and the viscoelastic creep occurs, over a period of from about 1 hour to about 24 hours. Usually, the tensile force applied will be constant, although this is not essential. Generally, if it is desired to impart a capacity to undergo a certain degree of viscoelastic contraction (in terms of percentage length of the suture thread), it will be necessary to cause the thread to undergo a degree of viscoelastic creep that is greater than the desired degree of viscoelastic contraction. The degree of viscoelastic creep necessary to impart a desired degree of viscoelastic contraction will depend on various factors including the material of the thread, the diameter, the degree of crystallinity, previous annealing conditions (if any) and the temperature employed during the viscoelastic creep. By way of example, the degree of viscoelastic creep may exceed the desired degree of viscoelastic contraction by a factor of from about 2 to about 10. An appropriate degree of viscoelastic creep can be determined easily by trial and error for any chosen conditions. Clearly, a thread should not be stretched to a point at which the thread fails and preferably the thread should not undergo significant permanent deformation.

Preferably, after the desired degree of viscoelastic creep has been achieved, the tensile force is released and the thread is allowed to undergo elastic contraction. The elastic contraction occurs almost instantaneously leaving the tendency to undergo viscoelastic contraction, which is a much slower process.

The tensile force is chosen, bearing in mind the material of the thread and the diameter of the thread, so as to achieve the desired degree of viscoelastic creep within a convenient time period, and without causing the thread to fail and preferably without the thread undergoing permanent deformation. Suitable forces can be readily determined by trial and error. By way of general guidance, the required tensile creep stress will be higher for smaller filament diameters. A typical stress may be in the region of about 50 MPa to about 200 MPa over a 24 hour time period, though a higher stress may be applied over a shorter period. The application of tensile stress to cause viscoelastic creep may be conveniently performed at ambient temperature (e.g. 20° C.).

For the present purposes, viscoelastic creep is measured as a percentage of the initial length of the thread that is used to manufacture the suture thread. On the other hand, viscoelastic contraction is measured as a percentage of the length of the suture thread at the start of the measurement (and not as a percentage of the initial length of the thread that is used to manufacture the suture thread). This is because, for a given suture thread which exists in a stressed state, the initial length of the thread that is used to manufacture the suture thread may not be known.

Preferably, the thread used to form the suture thread is subjected to a heat treatment (sometimes referred to as annealing) before it is subjected to viscoelastic creep. This may achieve two benefits. Firstly, prior heat treatment has been found in practice to increase the degree of viscoelastic contraction, and to increase the time over which viscoelastic contraction occurs, for a given degree of applied viscoelastic creep. Secondly, prior heat treatment may release existing stresses in the thread. This in turn means that the subsequent application of viscoelastic creep to the thread gives rise to a more reproducible degree of viscoelastic contraction. If a heat treatment is used, the temperature of the treatment will depend on the material of the thread. The temperature will, or course, be lower than the melting temperature, and it will be sufficient to achieve a relaxation of pre-existing stresses. Suitable temperatures and duration of heat treatment for any given thread material can be readily ascertained by trial and error. For many materials suitable for suture threads, a pre-treatment temperature of from about 100° C. to about 160° C. may be suitable. Suitable durations of heat pre-treatment may be in the range of from about tens of minutes to several hours. By way of example, the following heat treatment conditions have been found suitable for threads formed from the following polymers.

Nylon 6,6—heat treated at 150° C. for 30 minutes
Polypropylene—heat treated at 120° C. for 30 minutes
Ultra-high-molecular-weight polyethylene—heat treated at 120° C. for 30 minutes As discussed above, suture threads which undergo viscoelastic contraction in use may promote wound healing to a greater extent than known suture threads. In addition to the promotion of healing caused by application of force and movement to the wound tissue, and by the viscoelastic contraction bringing wound tissues into contact, wound healing may also be promoted by surface characteristics of the suture thread of the current invention. Specifically, it is believed that the process of applying to the thread the stressed state which gives the suture thread a tendency to undergo lengthwise viscoelastic contraction causes a modest decrease in surface hydrophobicity. A modest decrease in hydrophobicity may facilitate wound healing by causing migration of cells to the wound and causing cell proliferation.

In accordance with a fifth aspect of the invention, there is provided a viscoelastic solid substance, for use in a method of surgery as a surgical suture applied to a tissue which undergoes lengthwise viscoelastic contraction to apply a force to the tissue, wherein the viscoelastic substance is in the form of a thread which is in a state of stress which gives the thread a tendency to undergo lengthwise viscoelastic contraction.

BRIEF DESCRIPTION OF THE DRAWINGS

The following is a more detailed description, by way of example, of the preparation of suture threads which are in a stressed state so as to give the suture threads a tendency to undergo lengthwise viscoelastic contraction and of the manufacture of products comprising the threads, reference being made to the drawings in which.

DETAILED DESCRIPTION

Example 1

This example describes the manufacture of a first suture thread and the lengthwise viscoelastic contraction that is undergone by the first suture thread.

The first suture thread was manufactured from a nylon 6,6 monofilament thread having a diameter of 1.6 mm. The manufacture process consisted of: first subjecting the nylon 6,6 thread to a heat treatment; then subjecting it to a tensile force to cause viscoelastic creep; and finally releasing the tensile force to allow the thread to undergo elastic contraction so as to leave the thread in a stressed state with a tendency to undergo viscoelastic contraction.

The heat treatment (or annealing) was performed at a temperature of 150° C. for 30 minutes after which the thread was allowed to cool to ambient temperature.

The thread was then subjected to a tensile stress of 55 MPa for 20 hours at a temperature of 20° C. to 22° C. After this time, the thread had undergone viscoelastic creep so as to extend by 10.10% as a percentage of the initial thread length (i.e. final creep strain=10.10%).

Finally, the tensile force was released and the thread underwent elastic contraction, after which the remaining extension, as a percentage of the initial thread length, was approximately 7.2%.

Figure 1:
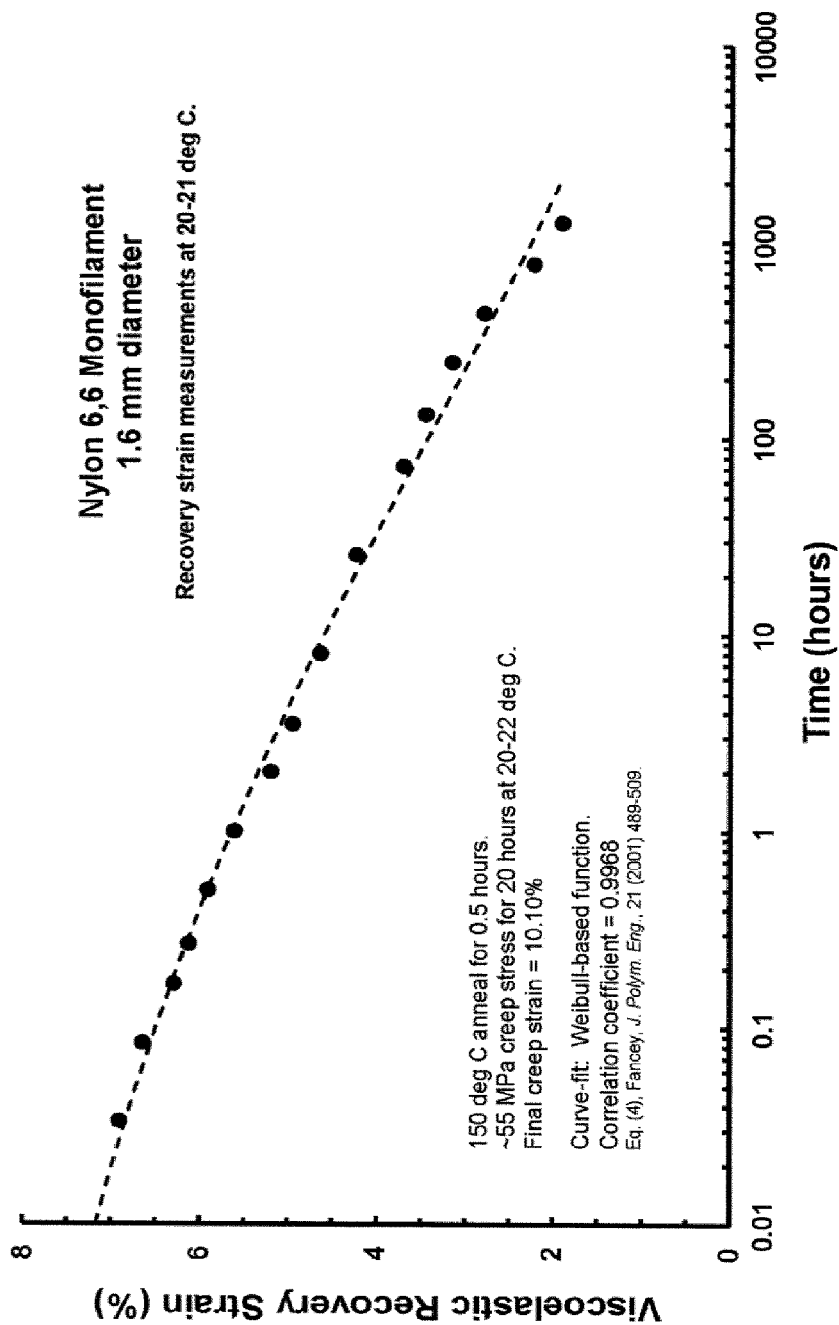
FIG. 1 is a graph showing viscoelastic contraction of a first suture thread.

As will be seen from FIG. 1, the first suture thread manufactured as described above, when left without application of force, at 20° C. to 21° C., underwent a degree of viscoelastic contraction of 5%-6% over a period of 1000 hours (equivalent to about 6 weeks). The degree of viscoelastic contraction is expressed as a percentage of the length of the suture thread (after manufacture as described above) and not as a percentage of the initial length of the thread used to manufacture the suture thread.

It will be appreciated that after manufacture of the suture thread, the suture thread may be packaged in a package as described above. Alternatively, or in addition, the suture thread may be engaged with a structure that maintains the tendency to undergo viscoelastic contraction, as described above. Both the suture thread and the structure may be packaged in a package. Alternatively, the structure may be part of a package.

Example 2

This example describes the manufacture of second and third suture threads and the lengthwise viscoelastic contraction that is undergone by the second and third suture threads.

The second suture thread according to the invention was manufactured from a polypropylene monofilament thread having a diameter of 0.3 mm, and sold by Ethicon US, LLC as Prolene (trade mark) EH7779 Blue Suture. The manufacture process consisted of first subjecting the polypropylene thread to a heat treatment; then subjecting it to a tensile force to cause viscoelastic creep; and finally releasing the tensile force to allow the thread to undergo elastic contraction so as to leave the thread in a stressed state with a tendency to undergo viscoelastic contraction.

The heat treatment (or annealing) was performed at a temperature of 120° C. for 30 minutes after which the thread was allowed to cool to ambient temperature.

The thread was then subjected to a tensile stress of 135.3 MPa for 24 hours at a temperature of 20° C. to 21° C. After this time, the thread had undergone viscoelastic creep so as to extend by 17.2% as a percentage of the initial thread length (i.e. final creep strain=17.2%).

Finally, the tensile force was released and the thread underwent elastic contraction, after which the remaining extension, as a percentage of the initial thread length, was approximately 9.4%.

Figure 2:
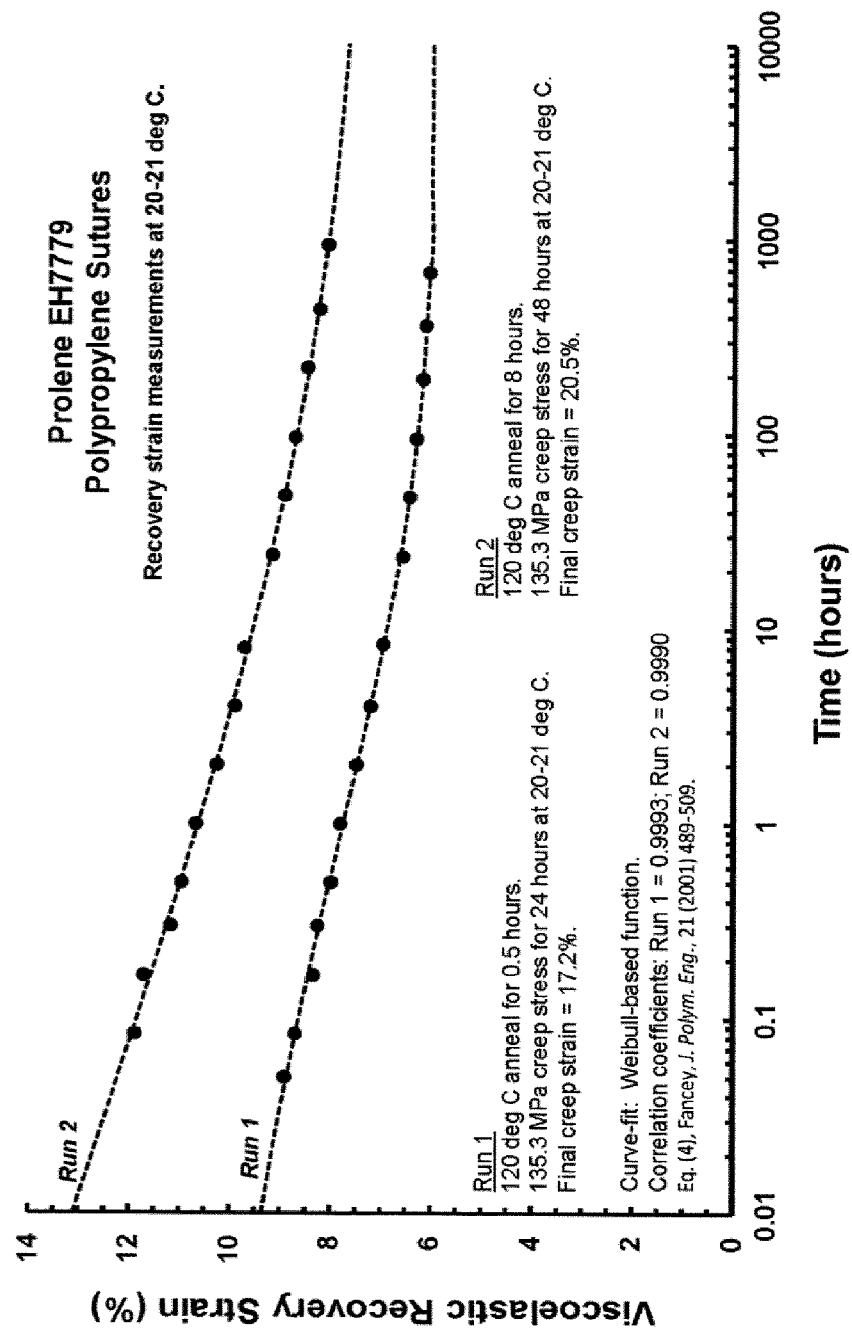
FIG. 2 is a graph showing viscoelastic contraction of second and third suture threads.

Viscoelastic contraction of the second suture thread is shown in FIG. 2 as Run 1. The second suture thread manufactured as described above, when left without application of force, at 20° C. to 21° C., underwent a degree of viscoelastic contraction of about 3.4% over a period of 1000 hours (equivalent to about 6 weeks). The degree of viscoelastic contraction is expressed as a percentage of the length of the suture thread (after manufacture as described above) and not as a percentage of the initial length of the thread used to manufacture the suture thread.

The third suture thread was manufactured from an identical polypropylene monofilament thread using a similar method to that described above in respect of the second suture thread. The only differences in the manufacture of the third suture thread were that the heat treatment (or annealing) was performed at a temperature of 120° C. for 8 hours (instead of 30 minutes) and that the polypropylene monofilament thread was then subjected to a tensile stress of 135.3 MPa for 48 hours (instead of 24 hours) at a temperature of 20° C. to 21° C. After this time, the thread had undergone viscoelastic creep so as to extend by 20.5% as a percentage of the initial thread length (i.e. final creep strain=20.5%).

The tensile force was then released and the thread underwent elastic contraction, after which the remaining extension, as a percentage of the initial thread length, was approximately 13.1%.

Viscoelastic contraction of the third suture thread is shown in FIG. 2 as Run 2. The third suture thread manufactured as described above, when left without application of force, at 20° C. to 21° C., underwent a degree of viscoelastic contraction of about 5.0% over a period of 1000 hours (equivalent to about 6 weeks). The degree of viscoelastic contraction is expressed as a percentage of the length of the suture thread (after manufacture as described above) and not as a percentage of the initial length of the thread used to manufacture the suture thread.

It will be appreciated that after manufacture of either the second or third suture thread, the suture thread may be packaged in a package as described above. Alternatively, or in addition, the suture thread may be engaged with a structure that maintains the tendency to undergo viscoelastic contraction, as described above. Both the suture thread and the structure may be packaged in a package. Alternatively, the structure may be part of a package.

Example 3

This example describes how the application of the stressed state appears to change the surface characteristics of the suture thread according to the invention.

Figure 3A:
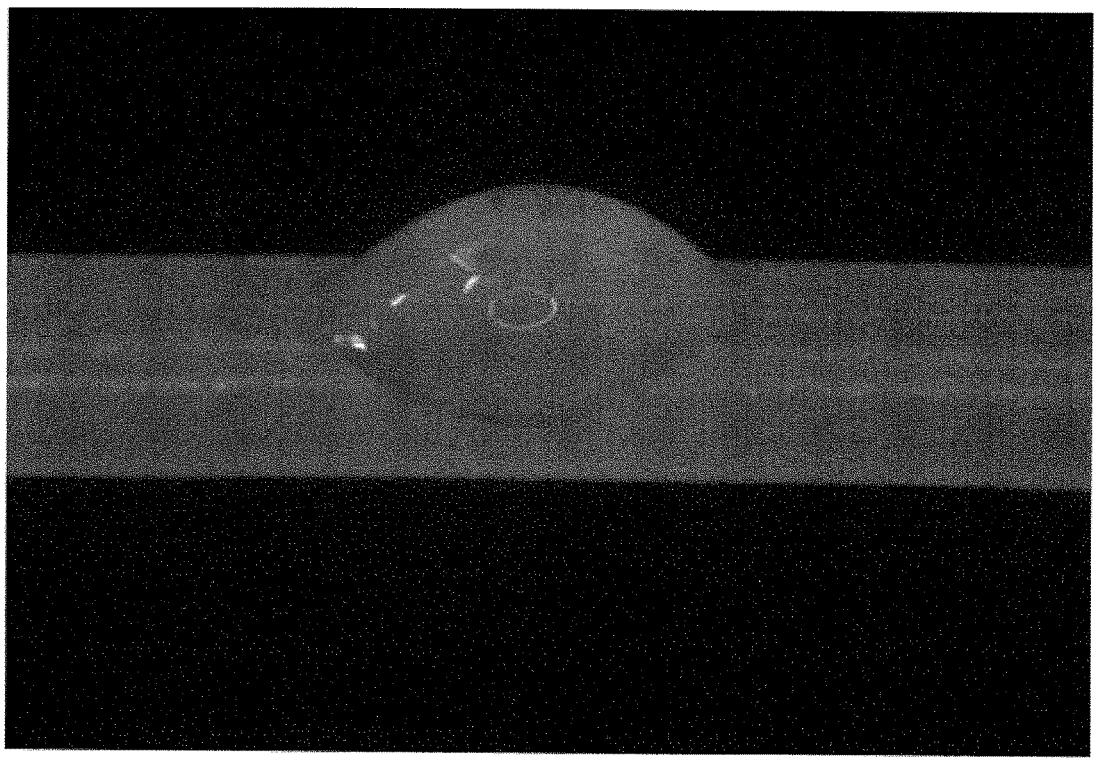
FIG. 3a is a photograph of a water droplet on a suture thread formed from nylon 6,6 which is in a stressed state so as to give the suture thread a tendency to undergo lengthwise viscoelastic contraction (the suture thread of FIG. 1)

FIG. 3a shows a nylon 6,6 suture thread prepared under the same conditions as used in Example 1 above, after relaxation of the elastic extension but before extensive viscoelastic contraction had occurred.

Figure 3B:
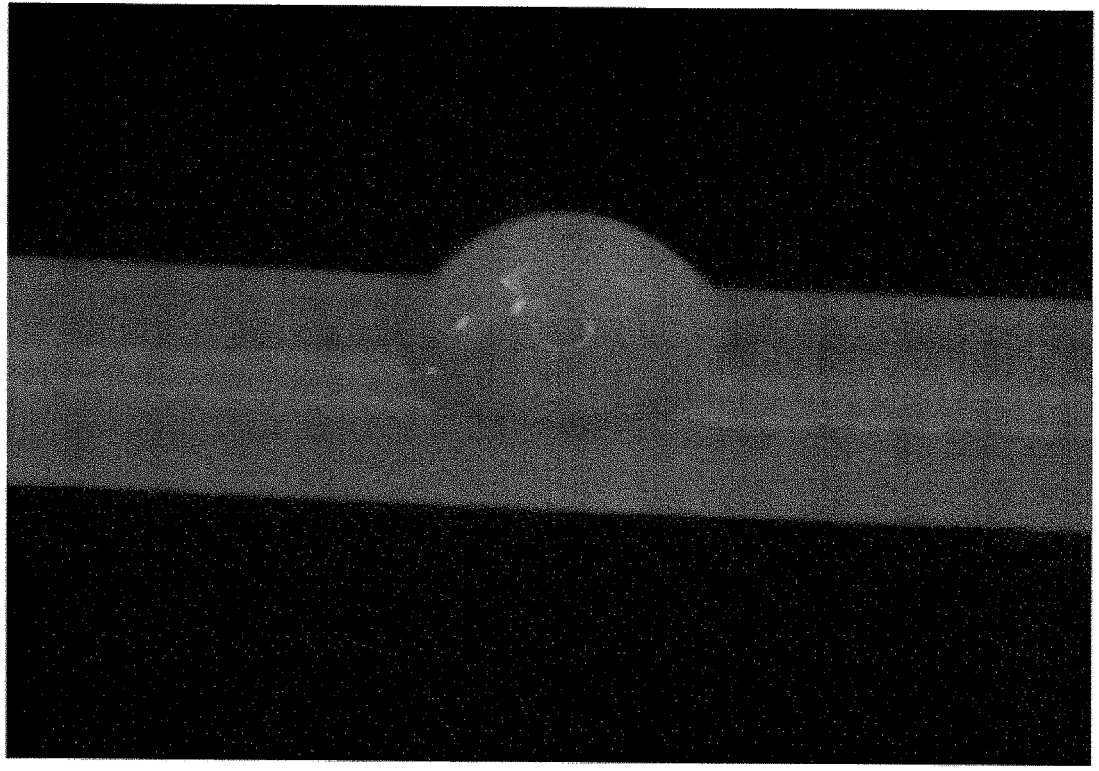
FIG. 3b is a photograph of a water droplet on a thread formed from nylon 6,6 which is not in a stressed state.

FIG. 3b shows a comparative nylon 6,6 thread (1.6 mm diameter monofilament) but which had not been subjected to viscoelastic creep.

FIGS. 3a and 3b show single water droplets on the respective nylon threads. The contact angle between the suture thread to which a stressed state had been applied as per Example 1 and its water droplet (FIG. 3a) was lower than the contact angle between the comparative nylon 6,6 thread and its water droplet (FIG. 3b). This suggests that the treatment used to apply the state of stress, and the tendency to undergo viscoelastic contraction, results in a modest decrease in the surface hydrophobicity.

Example 4

This Example demonstrates the capacity of the suture threads to apply a force as they undergo viscoelastic contraction.

Figure 4:
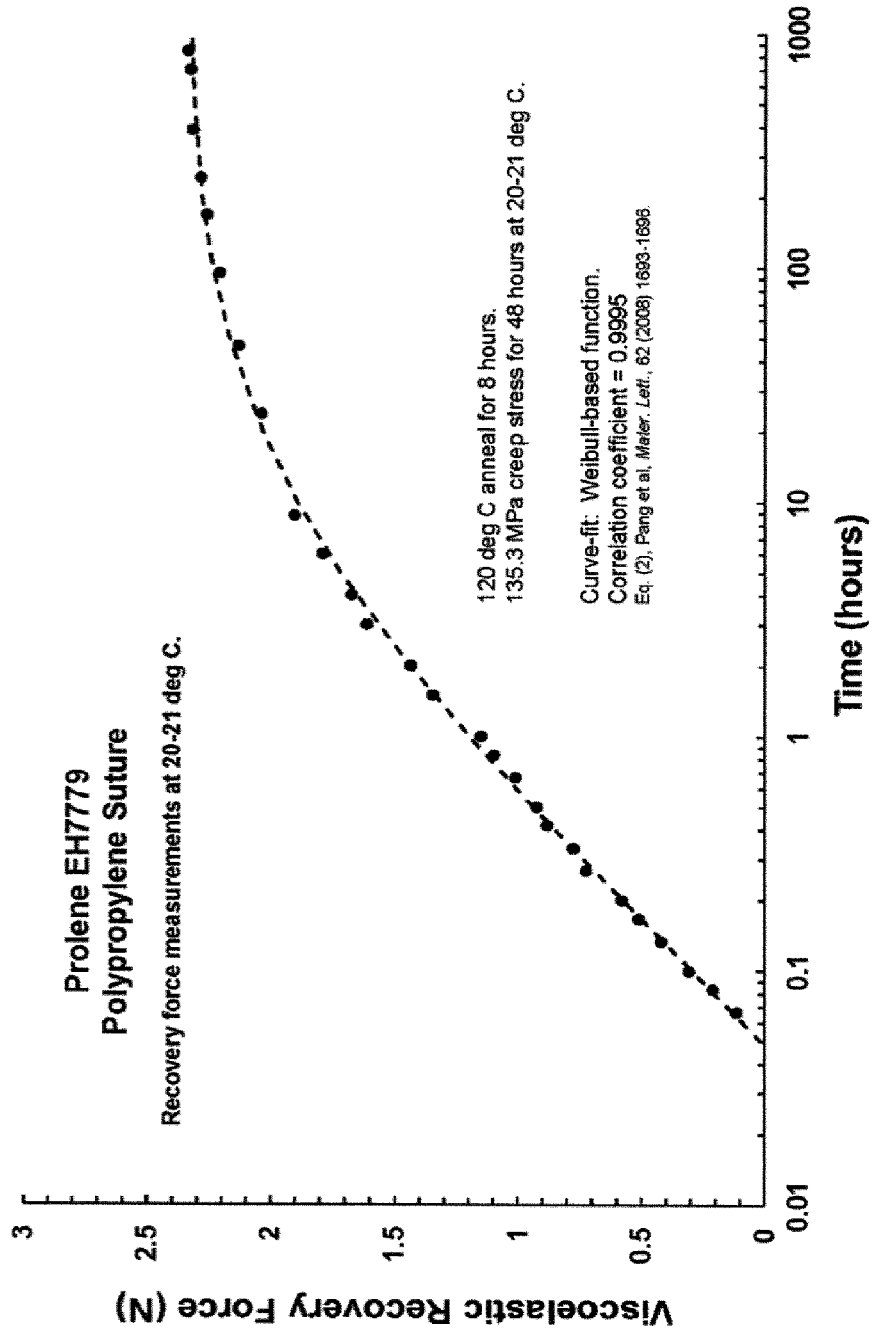
FIG. 4 is a graph showing force generated over time by a suture thread undergoing lengthwise viscoelastic contraction.
Figure 5:
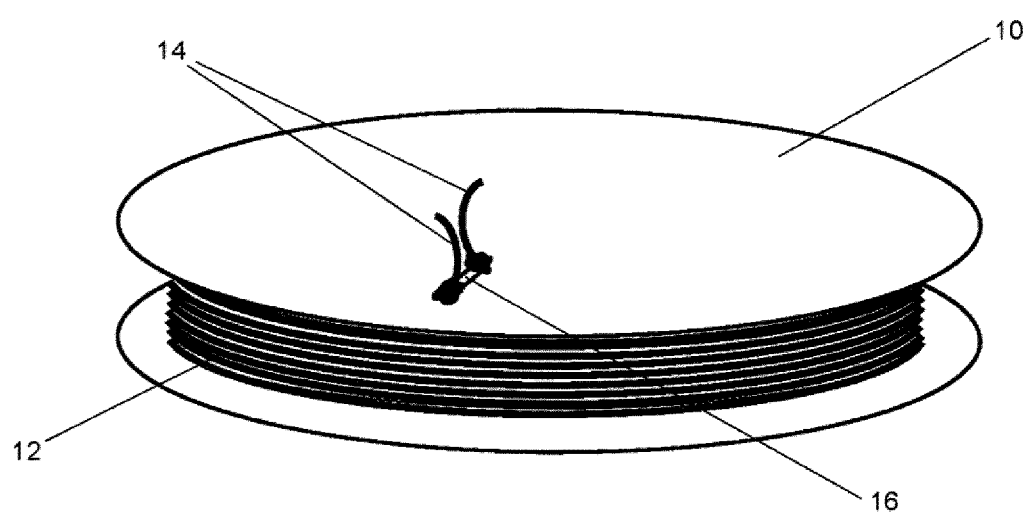
FIG. 5 is a schematic drawing of a suture thread engaged with a spool which maintains the suture thread in a stressed state.

A suture thread was formed into a loop by attaching the two ends to one another, having an overall (circular) length of about 60 cm. The heat treatment (or annealing) and tensile stress conditions were identical to the third suture thread described above. The loop was then placed around both a fixed support and the measurement point of a force gauge so that the loop was positioned, without appreciable tautness, between the fixed support and the attachment point. Force generated by the loop was measured over time at 20-21° C. The viscoelastic contraction of the loop was generally equivalent to the viscoelastic contraction of two lengths of suture thread, arranged in parallel to one another and each having a length approximately half that of the loop. The force was generated at a constant strain of 12% (as the fixed support and the attachment point of the force gauge were held substantially immobile relative to one another). It is believed that the length of the suture thread is not a major factor in the magnitude of the force. The results are shown in FIG. 4. As seen in FIG. 4, the generated force increased in a time dependent manner with the rate of increase of the force decreasing with time. After 100 hours the applied force was about 2.2 N.

Example 5

This example demonstrates the use of a structure to maintain the stressed state of the suture thread.

In this example, the structure is a simple spool 10. The suture thread 12 is wound around the spool 10 after the application of the stressed state. The two ends 14 of the suture thread are passed through a slot 16 in the spool 10. Each end 14 of the suture thread 12 is then knotted so as to fix the ends 14 to the spool 10 so that the spool 10 resists lengthwise viscoelastic contraction of the suture thread 12.

The invention claimed is:

1. A product comprising a suture thread and a package, the suture thread being sterile and being enclosed within the package so that the package maintains the suture thread sterile, the suture thread having a length, and being in a stressed state which gives the suture thread a tendency to undergo lengthwise viscoelastic contraction.

2. The product according to claim 1, wherein the suture thread is maintained in said stressed state by a structure engaged with the suture thread so as to resist lengthwise viscoelastic contraction of the suture thread by application of a force to the suture thread, the structure being disengageable from the suture thread to allow lengthwise viscoelastic contraction of the suture thread when it is desired to use the suture thread to form a surgical suture.

3. The product according to claim 2, wherein the structure is part of the package.

4. The product according to claim 1, wherein in the absence of externally applied force tending to resist lengthwise contraction and when maintained at a temperature of 20° C., the suture thread undergoes lengthwise viscoelastic contraction lasting over at least a period of time which is in the range of from 1 to 6 weeks, and wherein over said period of time the suture thread undergoes a degree of lengthwise viscoelastic contraction which is at least 1%, and preferably at least 2%, 3%, 4%, 5%, 6%, 7%, 8%, 9% or 10% of the length of the suture thread.

5. The product according to claim 1, wherein the suture thread is maintained in said stressed state by refrigeration.

6. The product of claim 1, wherein the tendency to undergo lengthwise viscoelastic contraction is such that when formed into a loop, the suture thread generates a force of at least 0.1 N, and preferably at least 0.2 N, 0.3 N, 0.4 N, 0.5 N, or 1 N over 100 hours at 20° C.

7. A product comprising a suture thread and a structure engaged with the suture thread, the suture thread having a length and two opposed ends, the suture thread being in a stressed state which gives the suture thread a tendency to undergo lengthwise viscoelastic, contraction, said engagement resisting lengthwise viscoelastic contraction of the suture thread by application of a force to the suture thread and comprising the suture thread being wound around a portion of the structure and the two ends of the suture thread being secured to the structure, the structure being disengageable from the suture thread to allow lengthwise viscoelastic contraction of the suture thread when it is desired to use the suture thread to form a surgical suture.

8. The product according to claim 7, wherein the structure is part of a package within which the suture thread is enclosed to maintain the suture thread sterile.

9. The product according claim 7, wherein in the absence of externally applied force tending to resist lengthwise contraction and when maintained at a temperature of 20° C., the suture thread undergoes lengthwise viscoelastic contraction lasting over at least a period of time which is in the range of from 1 to 6 weeks, and wherein over said period of time the suture thread undergoes a degree of lengthwise viscoelastic contraction which is in the range of from 1% to 30% of the length of the suture thread.

10. The product according to claim 9, wherein said lengthwise viscoelastic contraction over said period of time occurs at a rate which decreases over said period of time.

11. The product according to claim 9, wherein the degree of lengthwise viscoelastic contraction is in the range of 1% to 15%.

12. The product according to any one of claim 7, wherein in the absence of externally applied force tending to resist lengthwise contraction and when maintained at a temperature of 20° C., the suture thread undergoes lengthwise viscoelastic contraction lasting over at least a period of time which is in the range of from 1 to 6 weeks, and wherein over said period of time the suture thread undergoes a degree of lengthwise viscoelastic contraction which is at least 1%, and preferably at least 2%, 3%, 4%, 5%, 6%, 7%, 8%, 9% or 10% of the length of the suture thread.

* * * * *